(12) United States Patent
Sebti

(10) Patent No.: US 7,157,438 B2
(45) Date of Patent: Jan. 2, 2007

(54) RHOB AS A SUPPRESSOR OF CANCER CELL GROWTH AND CELL TRANSFORMATION

(75) Inventor: Said M. Sebti, Tampa, FL (US)

(73) Assignee: University of South Florida Board of Trustees, Tampa, FL (US)

(*) Notice: Subject to any disclaimer, the term of this patent is extended or adjusted under 35 U.S.C. 154(b) by 406 days.

(21) Appl. No.: 10/049,502

(22) PCT Filed: Jun. 18, 2001

(86) PCT No.: PCT/US01/19432

§ 371 (c)(1),
(2), (4) Date: Feb. 15, 2002

(87) PCT Pub. No.: WO01/97828

PCT Pub. Date: Dec. 27, 2001

(65) Prior Publication Data

US 2003/0018003 A1    Jan. 23, 2003

Related U.S. Application Data

(60) Provisional application No. 60/212,049, filed on Jun. 16, 2001.

(51) Int. Cl.
| | |
|---|---|
| A61K 37/70 | (2006.01) |
| A01N 43/04 | (2006.01) |
| C12Q 1/68 | (2006.01) |
| C12P 29/00 | (2006.01) |
| C12N 15/86 | (2006.01) |
| C12N 5/00 | (2006.01) |
| C12N 5/08 | (2006.01) |

(52) U.S. Cl. ............................. 514/44; 435/6; 435/455; 435/69.1; 435/456; 435/325; 435/366

(58) Field of Classification Search ................... 514/12; 435/6, 7.1, 7.8, 69.1; 530/350
See application file for complete search history.

(56) References Cited

U.S. PATENT DOCUMENTS

| | | |
|---|---|---|
| 2002/0034725 A1 | 3/2002 | McKenna et al. |
| 2004/0171547 A1 | 9/2004 | Sebti |

OTHER PUBLICATIONS

Chen et al Both Farnesylated and Geranylgeranylated RhoB Inhibit Malignant transformation and Suppress Human Tumor Growth in Nude Mice, JBC vol. 275(24) pp. 17974-17978, 2000.*
Liu and Jessell, A role for rhoB in the delamination of neural crest cells from the dorsal beural tube, Development, 1998, col. 125, pp. 5055-5067.*
Lebowitz et al, Farnesyltransferase Inhibitors Alter the Prenylations and Growth-stimulating Function of RhoB, JBC, 1997, vol. 272(25), pp. 15591-15594.*
Meng and El-Deiry, Tumor Suppressor Genes as Targets for Cancer Gene Therapy, Gene Therapy of Cancer, Chapter 1, pp. 3-18.*
Verma and Somia, Gene therapy-promises, problems and prospects, Nature, Sep. 1997, vol. 389, pp. 239-242.*
Marshall, Second Child in French Trial is FOund to Have aleukemia, Science, Jan. 2003, vol. 299, p. 320.*
Torchilin and Lukyanov, Peptide and protein drug delivery to and into tumors: challenges and solutions, Drug Discovery Today, Mar. 2003, vol. 8 pp. 259-265.*
Gura et al, Systems for Identifying New Drugs are Often Faulty, Sicence, 1997, vol. 278, pp. 1041-1042.*
McCormick, F. *Nature* 363: 15-16 (1993).
Campbell, S.L. et al., *Oncogene* 17:1395-1413 (1998).
Zohn, I.M., et al., *Oncogene* 17: 1415-1438 (1998).
Barbacid, M., *Annu. Rev. Biochem.*, 56:779-827 (1987).
Bos, J.L., *Cancer Res.* 49:4682-4689, (1989).
Olson, M.F., et al., *A. Science* 269:1270-1272 (1995).
Khosravi-Far, R. et al., *Mol. Cell. Biol.* 15:6443-6453 (1995).
Qiu, R. G., et al., *Nature* 374:457-459 (1995).
Mellor, H. et al., *J. Biol. Chem.* 273:4811-4814 (1998).
Jahner, D. et al., *Mol. Cell. Biol.* 11:3682-3690 (1991).
Fritz, G., et al., *J. Biol. Chem.* 270:25172-25177 (1995).
Zhang, F.L., et al., *Annu. Rev. Biochem.* 65:241-269 (1996).
Lebowitz, P.F., et al., *J. Biol. Chem.* 272:15591-15594 (1997).
Sebti, S.M., et al., *Pharmacol. Ther.* 74:103-114 (1997).
Gibbs, J.B., et al., *Annu. Rev. Pharmacol. Toxicol.* 37:143-166 (1997).
Cox, A.D., et al., *Biochem. Biophys. Acta* 1333:F51-F71 (1997).
Lebowitz, P.F., et al., *Oncogene* 17:1439-1445 (1998).
Chen, Z. et al., Farnesylated and Geranylgeranylated RhoB Suppress the Transformation of PANC-1 Human Pancreatic Concerl Cells; Proceedings of the 91st Annual Meeting of the American Association for Cancer Research, vol. 14, p. 220, abstract No. 1402.
Du, W. et al., Cell growth inhibition by farnesyltransferase inhibitors is mediated by gain of geranylgeranylated RhoB, Molecular and Cellular Biology, vol. 19, No. 3, Mar. 1999, pp. 1831-1840. g.
Chen, Z. et al. Both farnesylated and geranylgeranylated RhoB inhibit malignant transformation and suppress human tumor growth in nude mice, Journal of Biological Chemistry, vol. 275, No. 24, Jun. 16, 2000, pp. 17974-17978.

(Continued)

Primary Examiner—Dave Trong Nguyen
Assistant Examiner—Maria Marvich
(74) Attorney, Agent, or Firm—Saliwanchik, Lloyd & Saliwanchik

(57) ABSTRACT

The protein RhoB and its variants as a supressor of cancer cell growth, inhibitor of malignant cell transformation, and modulator of oncogenic signaling, wherein introducing RhoB directly, or indirectly via a nucleic acid, into a malignantly transformed cell or a cancerous cell decreases phosphorylation of Erk and Akt proteins inhibiting the PI3-kinase/Akt cell survival pathway and promoting apoptotic cell death. Methods and compositions are disclosed for administering to cancer patients, a prophylactic treatment to minimize the risk of malignant transformation, and advantageous combination of RhoB therapy with existing cancer treatments. The protein RhoB and the variants of the present invention are prenylated with either geranylgeranyl or farnesyl, and provision is made for selection of the prenylating moiety.

11 Claims, 4 Drawing Sheets

OTHER PUBLICATIONS

U.S. Appl. No. 10/759,328, filed Jan. 16, 2004, Sebti.

Adamson, P. et al. "Post-translational modifications of p21$^{the}$ proteins" *J Biol Chem*, 1992, 267:20033-20038.

Adnane, J. et al. "RhoB, not RhoA, represses the transcription of the transforming growth factor β type II receptor by a mechanism involving activator protein 1" *J Biol Chem*, 2002, 277:8500-8507.

Armstrong, S.A. et al. "CAAX geranylgeranyl transferase transfers farnesyl as efficiently as geranylgeranyl to RhoB" *J Biol Chem*, 1995, 270:7864-7868.

Baron, R. et al. "RhoB prenylation is driven by the three carboxylterminal amino acids of the protein: Evidenced *in vivo* by an anti-farnesyl cysteine antibody" *Proc Natl Acad Sci USA*, 2000, 97:11626-11631.

Chang, F. et al. "Signal transduction mediated by the Ras/Raf/MEK/ERK pathway from cytokine receptors to transcription factors: potential targeting for therapeutic intervention" *Leukemia*, 2003, 17:1263-1293.

Chardin, P. et al. "Coding sequence of human *rho* cDNAs clone 6 and clone 9" *Nucleic Acids Res.* 1988, 16: 2717.

Clark, E.A. et al. "Genomic analysis of metastasis reveals an essential role for RhoC" *Nature*, 2000, 406:532-535.

Downward, J. "Targeting Ras signaling pathways in cancer therapy" *Nat Rev Cancer*, 2003, 3:11-22.

Forget, M.A. et al. "The expression of Rho proteins decreases with human brain tumor progression: potential tumor markers" *Clin Exp Metastasis*, 2002, 19(1):9-15.

Fritz, G. and Kaina, B. "Ras-related GTPase RhoB represses NF-xB signaling" *J Biol Chem*, 2001, 276:3115-3122.

Fukata, M. et al. "Roles of Rho-family GTPases in cell polarisation and directional migration" *Curr Opin Cell Biol*, 2003, 15:590-597.

Genbank accession No. X06820, "H sapiens rhoB gene mRNA" Oct. 24, 1996.

Genbank accession No. CAA29968, "rhoB [*Homo sapiens*]" Oct. 24, 1996.

Jiang, K. et al. "Akt mediates Ras downregulation of RhoB, a suppressor of transformation, invasion, and metastasis" *Mol Cell Biol*, 2004, 24:5565-5576.

Jiang, K. et al. "EGFR, ErbB2 and Ras but not Src suppress RhoB expression while ectopic expression of RhoB antagonizes oncogene-mediated transformation" *Oncogene*, 2004, 23:1136-1145.

Liu, A-X, et al, "RhoB is dispensable for mouse development, but it modifies susceptibility to tumor formation as well as cell adhesion and growth factor signaling in transformed cells" *Mol Cell Biol*, 2001, 21:6906-6912.

Mazieres, J. et al. "Loss of RhoB expression in human lung cancer progression" *Clin Cancer Res*, 2004, 10:2742-2750.

Nakamura, T. et al. "Cloning of the RhoB gene from the mouse genome and characterization of its promoter region" *Biochem. Biophys. Res. Commun.*, 1996, 226(3):688-694.

Nobes, C.D. and Hall, A. "Rho, Rac, and Cdc42 GTPases regulate the assembly of multimolecular focal complexes associated with actin stress fibers, lamellipodia, and filopodia" *Cell*, 1995, 81:53-62.

Symons, M. and Rusk, N. "Control of vesicular trafficking by Rho GtPases" *Curr Biol*, 2003, 13:R409-418.

Wang, D-A and Sebti, S.M. "Palmitoylated cysteine 192 is required for RhoB tumor suppressive and apoptotic activities" Presentation at the American Association for Cancer Research, Anaheim, CA, Apr. 16-20, 2005, abstract.

Wang, D-A. and Sebti, S.M. "Palmitoylated cysteine 192 is required for RhoB tumor-suppressive and apoptolic activities" *J. Biol. Chem.*, 2005, 280:19243-19249.

Welsh, C.F. "Rho GTPases as key transducers of proliferative signals in $G_1$ cell cycle regulation" *Breast Cancer Res Treat*, 2004, 84:33-42.

U.S. Appl. No. 11/274,368, filed Nov. 14, 2005, Sebti.

Adnane, J. et al. "Suppression of Rho B expression in invasive carcinoma from head and neck cancer patients" *Clin Cancer Res*, 2002, 8:2225-2232.

Alimandi, M. et al. "Cooperative signaling of ErbB3 and ErbB2 in neoplastic transformation and human mammary carcinomas" *Oncogene*, 1995, 10:1813-1821.

Arboleda, M.J. et al. "Overexpression of AKT2/protein kinase Bβ leads to up-regulation of β1 integrins, increased invasion, and metastasis of human breast and ovarian cancer cells" *Cancer Res*, 2003, 63:196-206.

Buday, L. and Downward, J. "Epidermal growth factor regulates p21$_{the}$ through the formation of a complex of receptor, Grb2 adaptor protein, and Sos nucleotide exchange factor" *Cell*, 1993, 73:611-620.

Davies, M.A. et al. "Adenoviral-mediated expression of MMAC/PTEN inhibits proliferation and metastasis of human prostate cancer cells" *Clin Cancer Res*, 2002, 8:1904-1914.

Du, W. and Prendergast, G.C. "Geranylgeranylated RhoB mediates suppression of human tumor cell growth by farnesyltransferase inhibitors" *Cancer Res*, 1999, 59:5492-5496.

Forget, M.A. et al. "The expression of Rho proteins decreases with human brain tumor progression: potential tumor markers" *Clin Exp Metastasis*, 2002, 19(1):9-15, abstract.

Fritz, G. and Kaina, B. "*rhoB* encoding a UV-inducible Ras-related small GTP-binding protein is regulated by GTPases of the Rho family and independent of JNK, ERK, and p38 MAP kinase" *J Biol Chem*, 1997, 272(49):30637-30644.

Fritz, G. et al. "The Ras-related small GTP-binding protein RhoB is immediate-early inducible by DNA damaging treatments" *J Biol Chem*, 1995, 270(42):25172-25177.

Hall, A. "Rho GTPases and the actin cytoskeleton" *Science*, 1998, 279(5350):509-514.

Hunter, T. "Oncoprotein networks" *Cell*, 1997, 88:333-346.

Jiang, K. et al. "Regulation of Akt-dependent cell survival by Syk and Rac" *Blood*, 2003, 101:236-244.

Khosravi-Far, R. and Der, C.J. "The Ras signal transduction pathway" *Cancer Metastasis Rev*, 1994, 13:67-89.

Kim, D. et al. "Akt/PKB promotes cancer cell invasion via increased motility and metalloproteinase production" *Faseb J*, 2001, 15:1953-1962.

Kubiatowski, T. et al. "Association of increased phosphatidylinositol 3-kinase signaling with increased invasiveness and gelatinase activity in malignant gliomas" *J. Neurosurg*, 2001, 95:480-488.

Lebowitz, P.F. et al. "Evidence that farnesyltransferase inhibitors suppress Ras transformation by interfering with Rho activity" *Mol Cell Biol*, 1995, 15(12):6613-6622.

Liu, A. et al. "RhoB alteration is necessary for apoptotic and antineoplastic responses to farnesyltransferase inhibitors" *Mol Cell Biol*, 2000, 20(16):6105-6113.

Liu, A. et al. "RhoB is required to mediate apoptosis in neoplastically transformed cells after DNA damage" *Proc Natl Acad Sci USA*, 2001, 98(11):6192-6197.

Luetteke, N.C. et al. "mouse *waved-2* phenotype results from a point mutation in the EGF receptor tyrosine kinase" *Genes Dev*, 1994, 8:399-413.

Nakamura, T. et al. "Cloning of the RhoB gene from the mouse genome and characterization of its promoter region" *Biochem. Biophys. Res. Commun*, 1996, 226(3):688-694, abstract.

Park, B-K. et al. "Akt1 induces extracellular matrix Invasion and matrix metalloproteinase-2 activity in mouse mammary epithelial cells" *Cancer Res*, 2001, 61:7647-7653.

Pruitt, K. and Der, C.J. "Ras and Rho regulation of the cell cycle and oncogenesis" *Cancer Lett.*, 2001, 171(1):1-10.

Quilliam, L.A. et al. "Identification of residues critical for Ras(17N) growth-inhibitory phenotype and for Ras interaction with guanine nucleotide exchange factors" *Mol Cell Biol*, 1994, 14(2):1113-1121.

Stewart, A.L. et al. "P13K blockade by Ad-PTEN inhibits invasion and induces apoptosis in radial growth phase and metastatic melanoma cells" *Mol Med*, 2002, 8(8):451-461.

Symons, M. and Settleman, J. "Rho family GTPases: more than simple switches" *Trends Cell Biol*, 2000, 10(10):415-419.

Turkson, J. et al. "Requirement for Ras/Rac1-mediated p38 anc c-Jun N-terminal kinase signaling in Stat3 transcriptional activity induced by the Src oncoprotein" *Mol Cell Biol*, 1999, 19(11):7519-7528.

Van Aelst, L. and D'Souza-Schorey, C. "Rho GTPases and signaling networks" *Genes Dev*, 1997, 11(18):2295-2322.

Vlahos, C.J. et al. "A specific inhibitor of phosphatidylinositol 3-kinase, 2-(4-morpholinyl)-8-phenyl-4H-1-benzopyran-4-one (LY294002)" *J Biol Chem*, 1994, 269(7):5241-5248.

Yano, H. et al. "Biochemical and pharmacological studies with KT7692 and LY294002 on the role of phosphatidylinositol 3-kinase in FcεRI-mediated signal transduction" *Biochem J*, 1995, 312(Pt 1):145-150.

Pendergast and Rane "Farnesyltransferase inhibitors: mechanism and applications" *Expert Opin Invest Drugs*, 2001, 10(12):2105-2116.

Adjei, A.A. "Ras signaling pathway proteins as therapeutic targets" *Curr Pharm Design*, 2001, 7:1581-1594.

Caponigro, F. "Farnesyl transferase inhibitors: a major breakthrough in anticancer therapy?" *Anti-Cancer Drugs*, 13:891-897.

End, D.W. et al. "Characterization of the antitumor effects of the selective farnesyl protein transferase inhibitor R115777 *in vivo* and *in vitro*" *Cancer Res.*, 2001, 61:131-137.

Gura, T. "Systems for identifying new drugs are often faulty" *Science*, 1997, 278:1041-1042.

Kerbel, R.S. "Human tumor xenografts as predictive preclinical models for anticancer drug activity in humans" *Cancer Biol. & Ther.*, 2003, 2(4 Supp. 1):S134-S139.

Reuter, C.W. et al. "Targeting the Ras signaling pathway: a rational, mechanism-based treatment for hematologic malignancies?" *Blood*, 2000, 96:1655-1669.

Robson, T. and Hirst, D. "Transcriptional targeting in cancer gene therapy" *J. Biomed. Biotech.*, 2003, 2:110-137.

Shi, B. et al. "The farnesyl protein transferase inhibitor SCH66336 synergizes with taxanes in vitro and enhances their antihumor activity in vivo" *Cancer. Chemother. Pharmacol.*, 2000, 46:387-393.

Voskoglou-Nomikos, T. et al. "Clinical predictive value of the *in vitro* cell line, human xenograft, and mouse allograft preclinical cancer models" *Clin. Cancer Res.*, 2003, 9:4227-4239.

Sun, J. et al., "Antitumor efficacy of a novel class of non-thiol-containing peptidomimetic inhibitors of farnesyltransferase and geranylgeranyltransferase I: Combination therapy with the cytotoxic agents cisplatin, taxol, and gerncitabine" *Cancer Res.*, 1999, 59:4919-4926.

\* cited by examiner

RHOB AS A SUPPRESSOR OF CANCER CELL GROWTH AND CELL TRANSFORMATION

RELATED APPLICATIONS

This application is a National Stage Application of International Application Number PCT/US01/19432, filed Jun. 18, 2001, which claims the benefit of U.S. Provisional Application 60/212,049, filed Jun. 16, 2000, which is hereby incorporated by reference in its entirety.

STATEMENT OF SUPPORT

This work was supported by National Cancer Institute grant CA67771. Accordingly, the United States Government may have certain rights in the invention.

FIELD OF THE INVENTION

The present invention relates generally to the prevention, inhibition and treatment of cancer. More specifically, this invention relates to RhoB as a suppressor of cancer cell growth, as an inhibitor of malignant cell transformation, and as a modulator of oncogenic signaling. Even more specifically, the invention relates to variants of RhoB that are are prenylated with either geranylgeranyl or farnesyl, and to provision for selection of the prenylating moiety.

BACKGROUND AND SUMMARY OF THE INVENTION

Low molecular weight GTP/GDP binding GTPases such as Ras and Rho transduce mitogenic and survival signals from cell surface receptors to the nucleus. See, for example, McCormick, F. *Nature* 363: 15–16, (1993); Campbell, S. L., et al., *Oncogene* 17: 1395–1413, (1998); and Zohn, I. M., et al. *Oncogene* 17: 1415–1438, (1998). For example, platelet-derived growth factor (PDGF) and insulin-like growth factor-1 (IGF-1) stimulate cell proliferation and survival by activating their receptor tyrosine kinases, which recruit nucleotide exchange factors that activate Ras by converting it to its GTP-bound state. Once activated, Ras triggers a complex set of signal transduction pathways. These include the phosphatidylinositol-3-kinase/Akt pathway believed to be critical for cell survival, and the Raf/Mek/Erk kinase cascade that has been implicated in cell proliferation. In addition to its involvement in regulating proliferation and survival, Ras also plays a pivotal role in malignant transformation. In about 30% of all human cancers, Ras is mutated to a GTPase-deficient form that leads to constitutive activation of the above signaling pathways, uncontrolled proliferation, and survival of human tumors. Barbacid, M. *Annu. Rev. Biochem.* 56: 779–827, (1987); and Bos, J. L. *Cancer Res.* 49: 4682–4689, (1989). Family members (closely related) to Ras, such as RhoA and Rac1, have also been shown to be intimately involved in proliferation and transformation. For example, both RhoA and Rac1 are required for the G1 to S phase transition during the cell division cycle. Olson, M. F., et al., A. *Science* 269: 1270–1272, (1995). Furthermore, GTP-locked RhoA and Rac1 are transforming, and dominant negative forms of these GTPases inhibit Ras-induced malignant transformation. Khosravi-Far, R., et al., *Mol. Cell. Biol.* 15: 6443–6453, (1995) and Qiu, R.Get al., *Nature* 374: 457–459 (1995). Unlike RhoA and Rac1, less is known about the involvement of RhoB GTPase in proliferation and transformation. There are several features that distinguish RhoB from other Rho proteins. Firstly, its cellular localization within early endosomes and the pre-lysosomal compartment is different from the localization of other members. Mellow, H. et al., *J. Biol. Chem.* 273: 4811–4814, (1998). Secondly, RhoB is an immediate early response gene that is induced by PDGF, transforming growth factor-α, the non-receptor tyrosine kinase v-src, and ultraviolet irradiation. Jahner, D. et al., *Mol. Cell. Biol.* 11: 3682–3690, (1991), and Fritz, G., et al., *J. Biol. Chem.* 270: 25172–25177, (1995). However, these studies were mostly performed using fibroblasts, and whether RhoB is also an immediate early response gene in human cancer cells of epithelial origin is not known. Third and finally, RhoB mRNA and RhoB protein levels turn over much more rapidly (with half-lives of 20 and 120 min, respectively) than other GTPases, which typically have half lives on the order of 24 hrs. Therefore, although RhoA and RhoB share 90% amino acid sequence homology, their physiological functions are predicted to prefers a leucine. Ras proteins (e.g. H-, K- and N-Ras) are farnesylated, whereas RhoA and Rac1 are geranylgeranylated. Although RhoB has a C-terminal leucine, which would be predicted to dictate only geranylgeranylation, it is both farnesylated and geranylgeranylated in cells. Because Ras is constitutively activated in 30% of human cancers and Ras farnesylation is required for its malignant transforming activity, Lebowitz, P. F., et al., *J. Biol. Chem.* 272: 15591–15594, (1997), FTase inhibitors (FTIs) were designed as novel anticancer drugs. FTIs have shown impressive antitumor activity and lack of toxicity in preclinical models and are presently in various human clinical trial phases. Sebti, S. M., et al., *Pharmacol. Ther.* 74: 103–114, (1997); Gibbs, J. B., et al., *Annu. Rev. Pharmacol. Toxicol.* 37: 143–166, (1997); and Cox, A. D., et al., *Biochim. Biophys. Acta* 1333: F51–F71, (1997). Although FTIs were initially hypothesized to inhibit tumor growth by targeting Ras, recent evidence suggests that other farnesylated proteins may be involve, Lebowitz, P. F., et al., *Oncogene* 17: 1439–1445, (1998).

RhoB has been suggested as a potential candidate for several reasons. Firstly it is a substrate for FTase and FTIs inhibit its farnesylation, resulting in decreased RhoB-F and increased RhoB-GG. Secondly, RhoB's short half life more closely resembles the kinetics of FTIs reversal of transformation than Ras. Third, a RhoB/RhoA chimeric protein that is exclusively geranylgeranylated is growth inhibitory. Thereby, a myristylated form of RhoB which is not prenylated prevents FTIs from inhibiting Ras transformation. However, the biochemical properties of myristylated RhoB are not the same as wild type RhoB making it difficult to interpret the data. Furthermore, RhoB has been shown to be farnesylated by FTase as well as by GGTase I. Fourth and final, most of the studies carried out so far used murine fibroblasts. Therefore, although there is some evidence suggesting RhoB's involvement in FTIs antitumor activity, direct evidence implicating RhoB in FTIs mechanism of action in human tumors is lacking.

A novel function for RhoB(WT) as a potent inhibitor of malignant transformation and a suppressor of human tumor growth is disclosed herein. Furthermore, both RhoB-F and RhoB-GG induce apoptosis, inhibit oncogenic signaling and suppress transformation in vitro and in vivo. These findings demonstrate the tumor suppressing activity of RhoB, and strongly suggest that, contrary to prior suggestions, RhoB-F is not a target for FTIs in human cancer cells.

While the GTPase RhoA has been shown to promote proliferation and malignant transformation, RhoB's involvement in these processes is not well understood. RhoB is described herein as a potent suppressor of transformation and human tumor growth in nude mice. In several human cancer cell lines, RhoA promotes focus formation whereas RhoB is as potent as the tumor suppressor p53 at inhibiting transformation in this assay. It is demonstrated herein that both RhoB-F and RhoB-GG inhibit anchorage-dependent and -independent growth, induce apoptosis, inhibit constitutive activation of Erk and IGF-1 stimulation of Akt and suppress tumor growth in nude mice. The data demonstrate that RhoB is a potent suppressor of human tumor growth and that RhoB-F is not a target for farnesyltransferase inhibitors. RhoB therefore provides a novel target for therapeutic intervention in the treatment and prevention of cancer as disclosed herein.

DETAILED DESCRIPTION OF THE INVENTION

Figure 1:
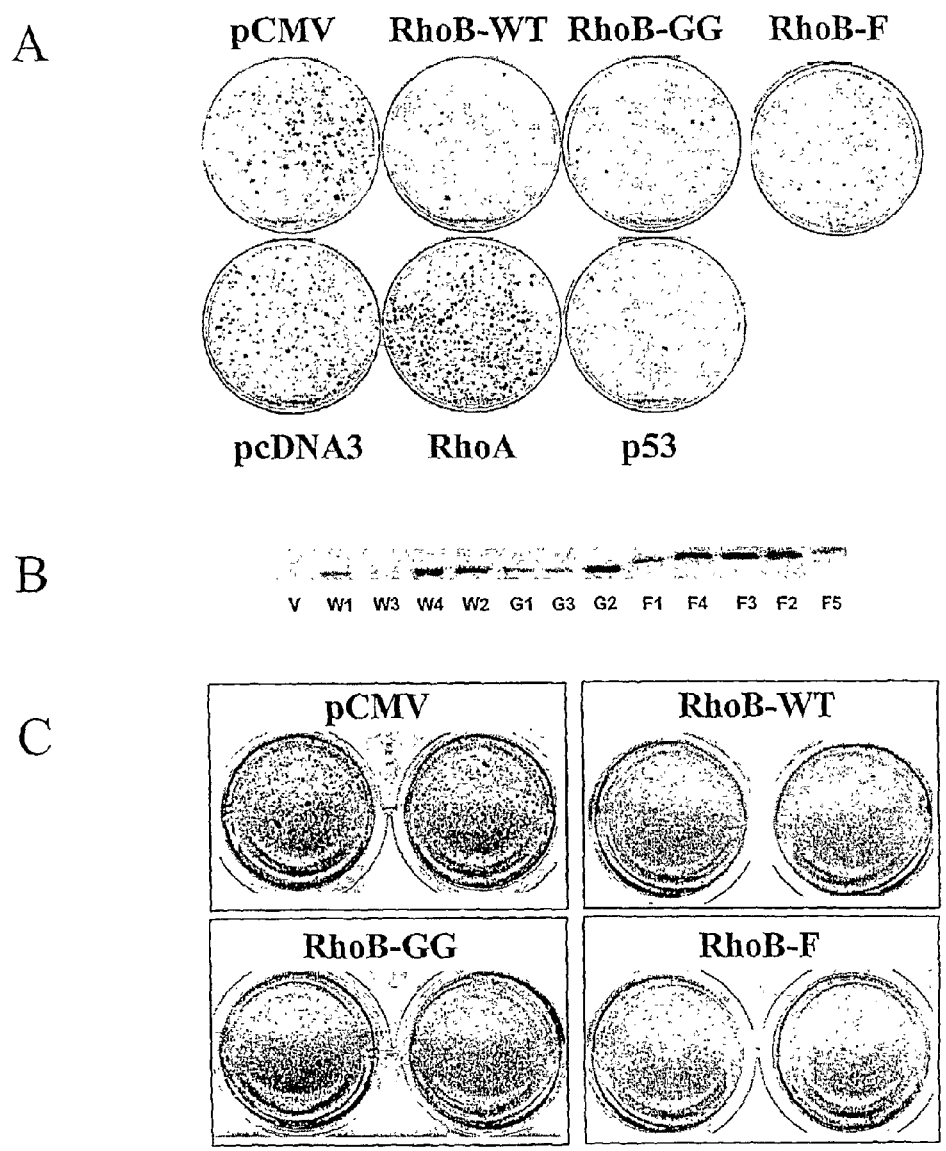
FIG. 1: RhoB-F, RhoB-GG and RhoB-WT are potent inhibitors of Panc-1 cell focus formation and soft agar growth. A. Focus formation. Panc-1 cells are transfected with the indicated expression vectors as described under Experimental-Procedures. Cells are maintained under drug selection for 2 weeks before being fixed and stained. Data are representative of two independent experiments carried out in duplicate. B. Several stably transfected Panc-1 cells expressing RhoB mutants are expanded and their levels of RhoB expression is determined by Western blotting as described under Experimental Procedures. V designates pCMV empty vector; W, F and G designate wild-type, farnesylated and geranylgeranylated RhoB mutants. C. Soft agar growth. Stably transfected Panc-1 cells (2000 cells/well) from clones W2, F2, G2 and V are plated in 12 well soft agar plates, fed twice a week and stained with MTT after 3 weeks as described under Experimental Procedures. Data are representative of 4 independent experiments.

In a general aspect, the present invention provides a method of inhibiting the growth of a cancerous cell, comprising contacting the interior of the cell with an effective amount of a RhoB protein or a variant thereof.

The formulations and methods of the present invention can be administered to treat a number of cancers, including but not limited to leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms'Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The method of the present invention is particularly applicable in the treatment of pancreatic tumors and lung cancer. The method of the present invention can be practiced on mammals, particularly humans.

The term "RhoB protein or a variant thereof" denotes RhoB-F, RhoB-GG and RhoB-WT proteins and any variants thereof that may be derived from RhoB-F, RhoB-GG or RhoB-WT as variants possessing at least one characteristic biological activity of RhoB, derived, for example, from the aforementioned proteins by truncation, oxidation, amino acid substitution, post-translational modification, labeling, or by linkage to another molecule.

In another embodiment, the invention provides a method of suppressing malignant transformation of a cell. In this embodiment, RhoB or a variant thereof a composition comprising RhoB, a variant of RhoB, or a pharmaceutically acceptable salt thereof is administered to a cell capable of malignant transformation, thereby preventing transformation. Thus, it will be apparent to one of skill in the art that the invention provides a method for preventing malignant transformation of a cell.

As demonstrated herein, the invention further provides a method of inducing apoptosis in a transformed cell. In this embodiment, RhoB or a variant thereof a composition comprising RhoB, a variant of RhoB, or a pharmaceutically acceptable salt thereof is administered to a transformed cell, thereby promoting apoptosis.

In a broader aspect, the invention therefore provides a method of inhibiting oncogenic signaling in a cell, and a method for decreasing phosphorylated protein such as Akt, Erk1, or Erk2 in a transformed cell, comprising administering to the cell a composition comprising RhoB, a variant of RhoB, or a pharmaceutically acceptable salt thereof.

The methods of the present invention, for example for inhibiting the growth of a cancerous cell, can be advantageously combined with at least one additional therapeutic method, including but not limited to chemotherapy, radiation therapy, therapy that selectively inhibits Ras oncogenic signaling, or any other therapy known to those of skill in the art of the treatment and management of cancer.

In one aspect, the method of the present invention is performed by introducing a nucleic acid construct encoding the RhoB protein or a variant thereof into the cell, whereby the RhoB protein, or variant thereof, is made within the cell from the construct. "Nucleic acid construct" refers to an assembly which is capable of directing the expression of the sequence(s) or gene(s) of interest. The construct preferably includes transcriptional promoter/enhancer or locus defining element(s), or other elements which control gene expression by other means such as alternate splicing, nuclear RNA export, post-translational modification of messenger, or post-transcriptional modification of protein. In addition, the construct preferably includes a sequence which, when transcribed, is operably linked to the sequence(s) or gene(s) of interest and acts as a translation initiation sequence. Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct preferably includes a packaging signal, long terminal repeats (LTRs), and positive and negative strand primer binding sites appropriate to the retrovirus used (if these are not already present).

Within one embodiment, a recombinant viral vector (preferably, but not necessarily, a recombinant MLV retrovirus) carries a vector construct containing a RhoB or variant RhoB gene expressed from an event-specific promoter, such as a cell cycle-dependent promoter (e.g., human cellular thymidine kinase or transferring receptor promoters), which will be transcriptionally active primarily in rapidly proliferating cells, such as tumors. In this manner, rapidly replicating cells which contain factors capable of activating transcription from these promoters are preferentially destroyed by the cytotoxic agent produced by the vector construct.

Administration of RhoB as a salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The protein variants of RhoB or nucleic acids that encode them can be formulated as pharmaceutical compositions and administered to a patient, such as a human patient, in a variety of forms adapted to the chosen route of administration, i.e., orally or parenterally, by intravenous, intramuscular, topical or subcutaneous routes, or via electroporation, or transformation. Additionally, naked DNA, or via virally mediated administration may be employed.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its slats can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No.4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 5–1500 mg, and may be administered, i.e., 1–3 times daily, to yield levels of about 0.1–50 mg/kg, for adults. A preferred dosage of the present invention is between 7.5 to 45 mg per day, administered orally, with appropriate adjustment for the body weight of an individual.

Accordingly, the invention includes a pharmaceutical composition comprising compounds as described above, or pharmaceutically acceptable salts thereof, in combination with a pharmaceutically acceptable carrier. Pharmaceutical compositions adapted for oral, topical or parenteral administration, comprising an amount of one or more of these compounds constitute a preferred embodiment of the invention. The dose administered to an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is-the amount which results in maximum inhibition of cancer, without unmanageable side effects.

The following examples further illustrate the present invention but, of course, should not be construed as in any way limiting its scope.

EXAMPLES

Experimental Procedures

Constructs. Wild type RhoB-WT which has a CKVL sequence for a CAAX box and which is both farnesylated and geranylgeranylated is used to make the following CAAX box mutants: RhoB-CAIM (F) designed to be only farnesylated and RhoB-CLLL (GG) designed to be only geranylgeranylated. All mutants are sequenced and found to have correct mutations. Also, all mutants are shown to have the correct prenylation status by transfecting each construct into COS7 cells, immunoprecipitating RhoB, cleaving the prenyl group and analyzing the nature of the prenyl by HPLC, see for example, Baron, R., et al., Proc Natl Acad Sci USA. 2000 Oct 10;97(21): 11626–31 "RhoB prenylation is driven by the three carboxyl-terminal amino acids of the protein: evidenced in vivo by an anti-farnesyl cysteine antibody." Wild type RhoA is subcloned into pCDNA3 by standard methods.

Focus Formation Assay. Panc-1, A549, and Saos-2 cell lines (ATCC) are derived from human pancreatic tumor, lung cancer, and osteosarcoma respectively. Hela and C33-A (ATCC) are derived from human cervical carcinoma. Panc-1, A549, Saos-2, C-33A and Hela are maintained in DMEM supplemented with 10% FBS. One day prior to transfection, $2 \times 10^5$ cells are seeded into 60 mm plates. Cells are transfected with 1 µg of each expression vector using Fugene6 (Boehringer Mannheim) following the manufacturer recommendations. Two days post-transfection cells are collected with trypsin, counted and seeded into 100 mm plates at a density of $5 \times 10^4$ per plate. RhoA and p53 are expressed from pCDNA3/neo vector (Invitrogen) whereas RhoB-wt, RhoB-F and RhoB-GG from pCMV-IRES/Zeo vector. Zeocin (Invitrogen) is used as a selection drug for cells transfected with RhoB expression vectors and G418 (Mediatech, Inc.) for cells transfected with RhoA and p53. Zeocin is used at a concentration of 300 µg/ml for Panc1, and A549, and 150 µg/ml for Hela, Saos-2 and C-33A, whereas G418 at a concentration of 800 µg/ml for Panc-1 and 400 µg/ml for Hela, Saos-2 and C-33A. Cells are cultured in presence of selection drug for 2 weeks before being fixed and stained with KaryoMax Giemsa Stain (GibcoBRL). Briefly, the medium is discarded and cells washed once with PBS and once with PBS:methanol (1:1). 50% of methanol/PBS mixture is replaced with fresh methanol and left for 10 min. The mixture is discarded and cells are washed with fresh anhydrous methanol. The monolayer is then covered with Giemsa stain for 2 min. Finally, the stain is displaced with water.

Generation of stably transfected Panc-1 cells. Panc-1 or A549 cells are grown in DMEM/10%FBS. Different RhoB constructs (RhoB-F, RhoB-GG, RhoB-F/GG) and the corresponding empty vector are transfected to Panc-1 cells by using calcium phosphate method. At day 0, panc-1 cells are plated ($1.7 \times 10^5$ cells/plate), RhoB mutant constructs are transfected (Day 1) and growth medium is changed (Day 2). Cells are split (Day 3) and fresh growth medium containing selection marker, Zeocin (300 μg/ml) is changed every 3–4 days, until colonies formed two weeks later. Stably transfected cell lines are expanded and frozen in liquid nitrogen for future use.

Soft agar assay is carried out as described by Sun, J., et al., *Cancer Res.* 59: 4919–4926, (1999).

Anchorage-dependent growth. Stably transfected Panc-1 or A549 cells expressing the different RhoB mutants are plated in 10% FBS. The number of cells in each dish is counted on days 1, 4, 5, 6 and 7. Cells are counted by hemacytometer.

Apoptotic assay. To analyze cells undergoing apoptosis, the TdT digoxygenin nick end-labeling with ApopTag Fluorescein In Situ Apoptosis Detection Kit is used. Cells are trypsinized, washed with PBS and fixed in 1% paraformaldehyde in PBS. After cytospin and washes with PBS, TdT Enzyme is applied to the cells followed by anti-Digoxigenin-fluorescein. Mounting medium containing Dapi is used to counterstain the nuclei. The cells are viewed by fluorescent microscopy.

Western-blot analysis. Panc-1 or A549 cells stably expressing different RhoB constructs are grown in DMEM/0.5%FBS for 48 hs, treated with or without IGF-1 (50 ng/ml) and processed for Western blotting as described by Sun et al. supra. Phospho AKT is analyzed by using anti-phospho AKT antibody (N.E.Biolabs). Phospho-erk is detected by anti-phospho-erk1/erk2 antibody (N.E.Biolabs). Non-phosphorylated Akt and erk-2 are detected by anti-Akt (Santa Cruz Biotechnology) and anti-erk2 (Upstate Biotechnology). RhoB protein is detected by mouse monoclonal anti-RhoB antibody (Santa Cruz). For phospho-Akt and phospho-erk2, bands are quantified by using a scanning densitometer Model IGS-700 (BioRad).

Nude mouse tumor xenograft model. Nude mice (Harlan Sprague Dawley, Indianapolis, Ind.) are maintained in accordance with the Institutional Animal Care and Use Committee (IACUC) procedures and guidelines. Panc-1 cells stably expressing RhoB-WT, RhoB-GG, RhoB-F and empty vector are harvested, resuspended in PBS and implanted s.c. into the right and left flank ($10 \times 10^6$ cells per flank) of 8 week old female nude mice and the tumors measured as described previously (20). Statistical significance between empty vector and different stably-transfected RhoB mutants are evaluated by using Student's t-test ($p<0.05$).

Results and Discussion

RhoB-F, RhoB-GG, RhoB-WT and p53, but not RhoA, suppress focus formation of several human cancer cell lines. To illustrate the suppression of transformation by both RhoB-F and RhoB-GG, CAAX box mutants of RhoB are generated that are either exclusively farnesylated or geranylgeranylated. To illustrate the effects of the RhoB mutants on transformation of human cancer cells, both in vitro and in vivo assays are used. The effects of the RhoB mutants on the ability of human cancer cells to grow foci in a focus formation assay are first shown. Several human cancer cell lines are transfected with the RhoB mutant DNAs and the foci that formed are scored 14 days later. Control transfections are also performed with the tumor suppressor p53 and the GTPase RhoA, a closely related RhoB family member that shares 90% amino acid homology. FIG. 1A and Table 1 show that the human pancreatic cancer cell line, Panc-1, transfected with empty vector DNA, pCMV, forms numerous foci (155–233 foci). In contrast, Panc-1 cells transfected with wild type RhoB grow only 23–39 foci. Furthermore, RhoA-transfected Panc-1 cells grow more foci (over 346–409) than pcDNA3 empty vector-transfected cells (163–211 foci) (FIG. 1A and Table 1). In contrast, Panc-1 cells transfected with p53 far fewer foci (21–27 foci). This illustrates that whereas RhoA promotes, RhoB suppresses foci formation, and thus RhoB is capable of antagonizing transformation of Panc-1 cells. The prenylation status of RhoB does not affect its ability to inhibit foci formation of Panc-1 cells. FIG. 1A and Table 1 show that RhoB-P and RhoB-GG are also potent inhibitors of Panc-1 foci formation. Whether this inhibition of foci formation by RhoB can be extended to human cancer cells without Ras mutations is now determined. Table 1 shows that RhoB-F, RhoB-GG and RhoB-WT are potent inhibitors of foci formation of C33A and Hela (cervical carcinomas), and Saos-2 (osteosarcoma) none of which express mutated Ras. In all of these cell lines, p53 inhibited whereas RhoA promoted foci formation (Table 1).

Similar results are obtained using A549 lung carcinoma cells in place of Panc-1 cells.

Both RhoB-F and RhoB-GG as well as RhoB-WT inhibit anchorage-independent and anchorage/dependent growth of Panc-1 cells. To illustrate the effects of the RhoB mutants on malignant transformation, Panc-1 or A549 cells are transfected with the above constructs and several stable clones are isolated. Expression of RhoB is controlled by Western blotting using several clones picked from each construction (FIG. 1B). Representative clones are selected for further studies. The clones picked for further study are RhoB-WT clone 2 (W2), RhoB-F clone 2 (F2) and Rho-GG clone 2 (G2) (FIG. 1B). The effects of the different RhoB mutants on the ability of Panc-1 or A549 cells to grow on soft agar is now shown. Panc-1 or A549 cells stably-transfected with either empty vector, RhoB-F, RhoB-GG or RhoB-WT are plated on soft agar plates and developed 3 weeks later. FIG. 1C shows that Panc-1 cells transfected with empty vector grow numerous large colonies. In contrast, Panc-1 or A549 cells expressing RhoB-WT, RhoB-F and RhoB-GG show little growth on soft agar. RhoB wild type is very potent at inhibiting Panc-1 soft agar growth and no colonies are detected (FIG. 1C). Thus, the results of FIG. 1C agree with those of FIG. 1A and Table 1 and demonstrate that RhoB antagonizes tumor growth and further suggest that RhoB-F is not a target for FTIs' antitumor activity in human cancer cells.

Figure 2:
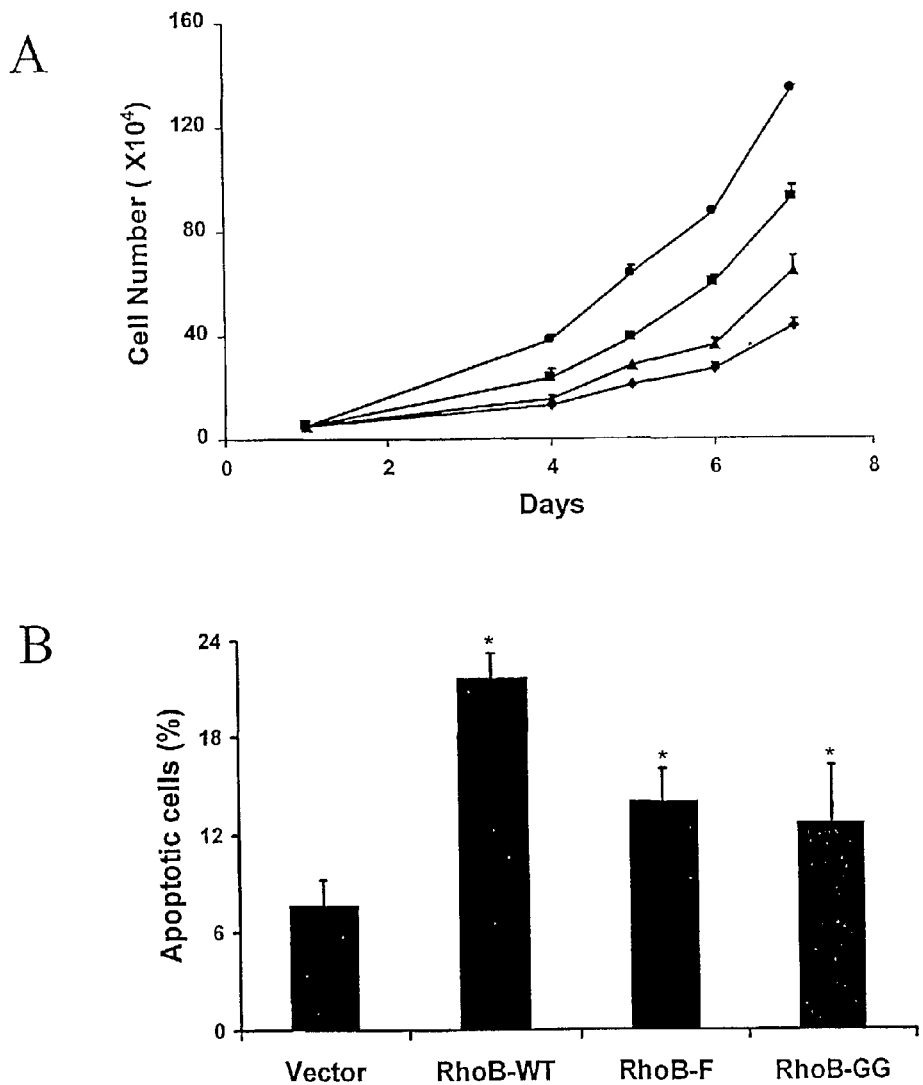
FIG. 2: RhoB inhibits anchorage-dependent growth and induces apoptosis in Panc-1 cells. A. Panc-1 cells stably transfected either with empty vector (●), RhoB-GG (▲), RhoB-F (■) or RhoB-WT (♦) are plated in 60 mm plates ($1.7 \times 10^5$ cells/plate). The cells are then harvested at days 0, 5, 7 and 8 and counted. Data are representative of three independent experiments. B. Panc-1 cells stably expressing RhoB-WT, RhoB-F, RhoB-GG or empty vector (pCMV) are plated in 10% FBS on day 1, harvested on day 3 and processed for ApopTag apoptosis assay as described under Experimental Procedures. The number of cells undergoing apoptosis are counted. About 500 cells are counted for each cell line. The percentage of apoptotic cells is determined as the percentage of bright green cells among the total number of cells. Data represent the average numbers and standard error of 3 independent experiments. * designates $p<0.05$ between pCMV and the various mutants.

Anchorage-dependent and anchorage-independent growth in Panc-1 or A549 cells could be regulated by different mechanisms. The effect of the RhoB mutants on the anchorage-dependent growth of Panc-1 cells is therefore shown. The different Panc-1 cell lines are plated on plastic dishes and the growth rate of each cell line is determined by counting cells for 7 days. FIG. 2A shows that empty vector Panc-1 cells grow the fastest and reach $1.34 \times 10^6$ cells over 7 days. In contrast, RhoB-WT cells grow the least and reached only $0.43 \times 10^6$ cells over the same period of time. RhoB-F and RhoB-GG also grow more slowly, reaching $0.64 \times 10^6$ and $0.93 \times 10^6$ cells after 7 days. Thus, RhoB inhibits both anchorage-dependent and -independent growth of Panc-1 cells, but the effect on anchorage-independent growth is more pronounced for all mutants. Comparable results are obtained using A549 cells.

RhoB-F, RhoB-GG and RhoB-WT induce apoptosis with little effect on cell cycle distribution. The ability of RhoB mutants to inhibit anchorage-dependent and anchorage-independent growth could be due to cell cycle arrest and/or apoptosis. The inability of RhoB mutants to alter cell cycle distribution by flow cytometry is thus illustrated. It is shown RhoB mutants have little effect on cell cycle distribution (data not shown). It is next shown using ApopTag DNA fragmentation assays that the RhoB mutants affect programmed cell death of Panc-1 or A549 cells. FIG. 2B shows that only 7% Panc-1 cells transfected with empty vector are undergoing apoptosis. In contrast, 21, 14 and 13% of RhoB-WT, RhoB-F and Rho-GG cells, respectively, are apoptotic. Thus, RhoB mutants enhance the ability of Panc-1 and A549 cells to undergo apoptosis by 2 to 3-fold. RhoB-wt is most potent at inducing apoptosis.

Figure 3:
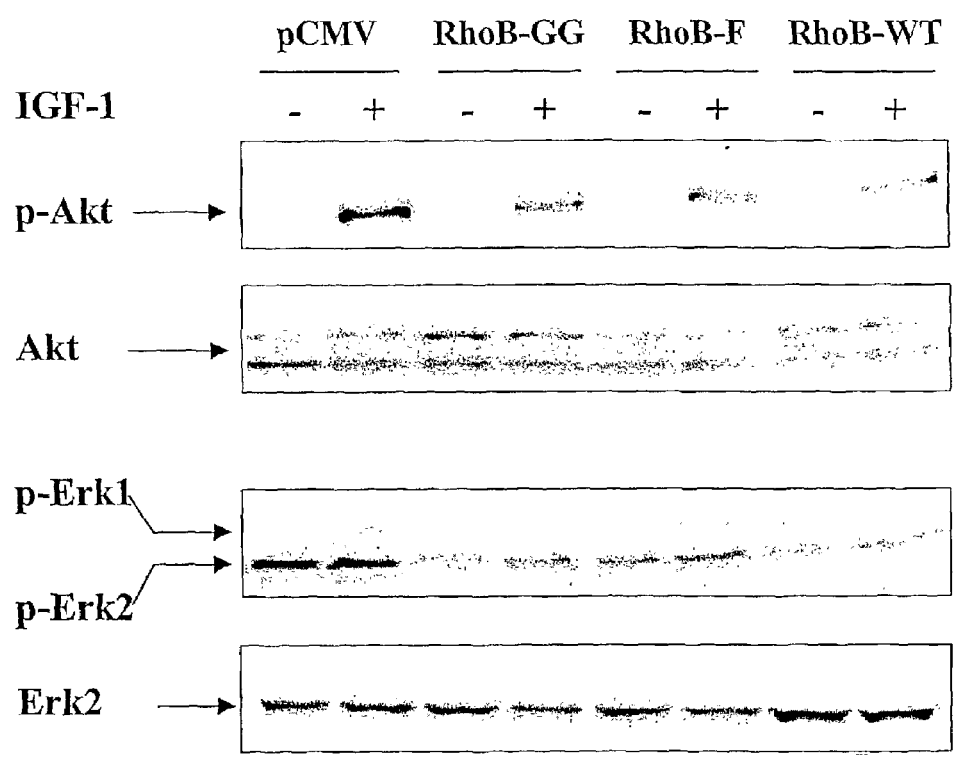
FIG. 3: RhoB inhibits IGF-1-stimulated Akt and constitutive activation of Erk2. Stably-transfected Panc-1 cells are plated on day 1 in 10% FBS and starved (0.5% FBS) on day 2 for 48 hrs. The cells are then treated with IGF-1 for 10 min, harvested, the lysates (25 μl/lane) separated on a 10% SDS-PAGE as described under Experimental Procedures. After transfer to nitrocellulose, the samples are immunoblotted with either a phospho-specific antibody against Akt or Erk1/Erk2. Expression levels of Akt and erk2 are also analyzed by anti-Akt and anti-erk2 antibodies, respectively. The data are representative of 4 independent experiments (phospho-Akt and phospho-erk1/erk2) and 2 independent experiments (Akt and erk2 expression levels).

RhoB-F, RhoB-GG and RhoB-WT inhibit IGF-1 stimulation of Akt and constitutive activation of Erk1/Erk2. A possible mechanism by which RhoB would enhance the ability of Panc-1 or A549 cells to undergo apoptosis is by inhibiting a survival pathway. One of the major signal transduction pathways that contributes to cell survival and prevention of cell death is the growth factor-stimulated P13-kinase/Akt pathway, in which the ser/thr kinase Akt plays a pivotal role. Thus, the effects of the various RhoB mutants on the ability of one of the major survival growth factors, IGF-1, to stimulate Akt is shown by Western immunoblotting with an antibody specific for activated (phosphorylated) Akt. FIG. 3 shows that IGF-1 treatment of serum-starved Panc-1 cells transfected with empty vector results in potent activation of Akt. In contrast, in Panc-1 or A549 cells overexpressing RhoB-F, RhoB-GG and RhoB-WT, the ability of IGF-1 to stimulate AKT phosphorylation/activation is inhibited by 50% (±16%), 50% (±18%) and 65% (±15%), respectively. None of the RhoB mutants affect the expression levels of Akt (FIG. 3).

The effects of the RhoB mutants on the activation of Erk1 and Erk2 is next illustrated. These experiments are carried out as for the experiments described above for AKT, except that activation of Erk1/Erk2 is determined by immunoblotting using an antibody specific for activated (phosphorylated) Erk1/Erk2. Unlike Akt, treatment with IGF-1 does not further stimulate erk1 and erk2 (FIG. 3). Furthermore, in Panc-1 or A549 cells erk2, but not erk1, is constitutively activated as is apparent from the strong hyperphosphorylated band. FIG. 3 shows that RhoB-WT, RhoB-GG and RhoB-F inhibit erk2 constitutive activation by 75%, 70% and 60%, respectively. None of the RhoB mutants affect the expression levels of erk2 (FIG. 3).

Figure 4:
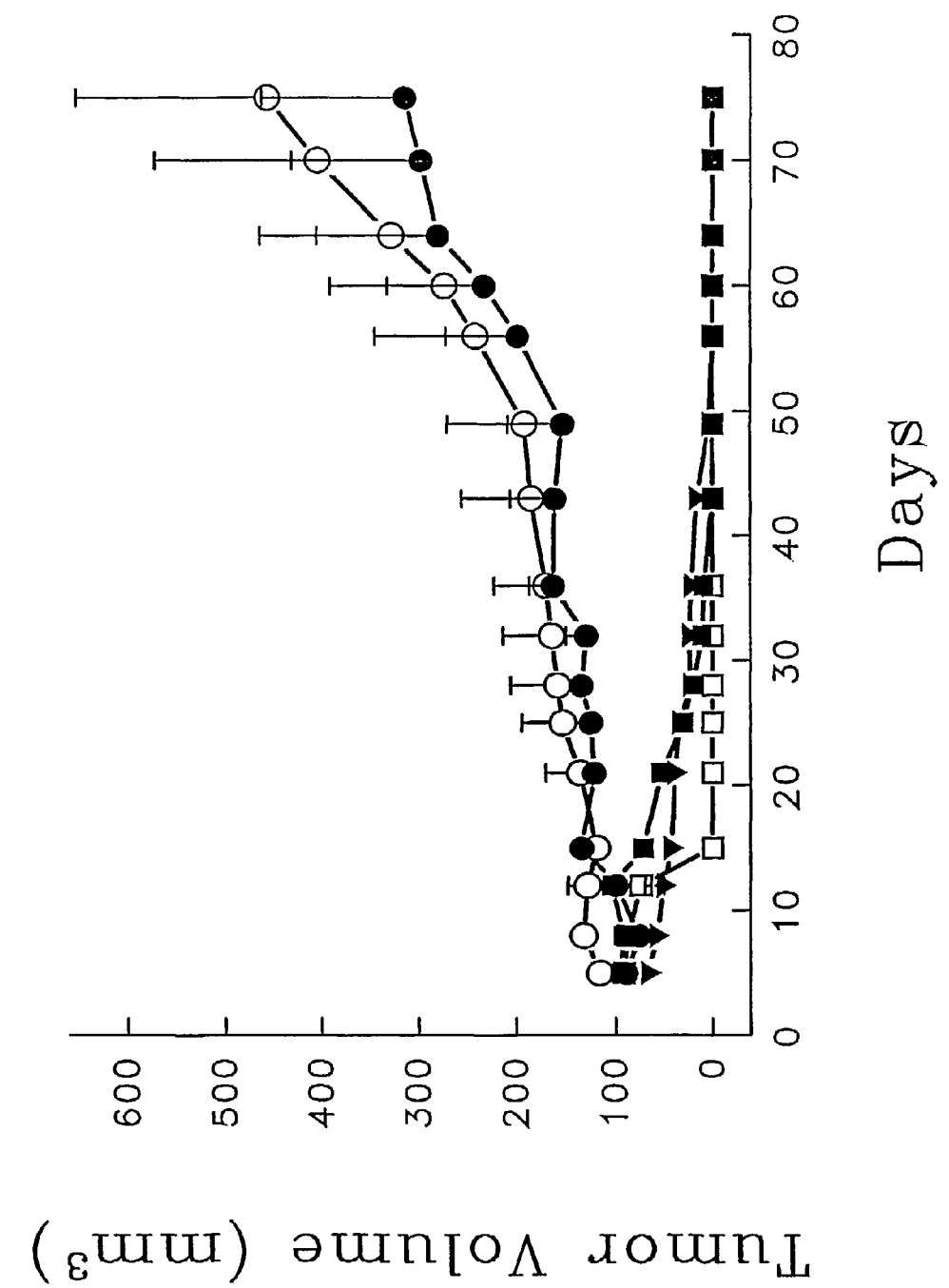
FIG. 4: RhoB-F, RhoB-GG and RhoB-WT suppress Panc-1 tumor growth in nude mice. Stably-transfected Panc-1 cells that express either RhoB-ΔBox (●), RhoB-F (■), RhoB-GG (▲), RhoB-WT (□) or empty vector (○) are implanted s.c. in nude mice and the tumor sizes measured over time as described under Experimental Procedures. Bars represent standard errors. The data is representative of three independent experiments (RhoB-F, RhoB-GG and RhoB-WT) and two independent experiments (RhoB-ΔBox).

RhoB-F, RhoB-GG and RhoB-WT suppress the growth of Panc-1 tumor cells in nude mice. The above illustrations show that RhoB inhibits proliferation, foci formation and soft agar growth, induces apoptosis and inhibits signal transduction pathways involved in survival and transformation. The data indicate that RhoB is a potent suppressor of malignant transformation in Panc-1 or A549 cells in vitro. The ability of the RhoB mutants to suppress malignant transformation in vivo is illustrated next by showing their effects on the growth of Panc-1 cells in nude mice. Panc-1 cells expressing the different RhoB mutants ($10^7$ cells/per flank) are implanted s.c. under the right and left flank of nude mice. The tumor growth of the different Panc-1 cells is then followed by caliper measurements of the tumor sizes over time as described under Experimental Procedures. FIG. 4 shows that within 5 days of cell implantation under the skin of nude mice, empty vector Panc-1 cells had an average tumor size of 116±10. In contrast, cells stably expressing RhoB-GG, RhoB-WT or RhoB-F are smaller and flatter in appearance and have an average tumor size of 67±6, 91±9 and 95±8 mm, respectively. FIG. 4 also shows that empty vector cells grow whereas RhoB-WT, RhoB-F and RhoB-GG expressing Panc-1 cells regress. Tumor regression is the fastest with Panc-1 cells stably expressing RhoB-WT. Within 15 days of tumor implantation, all tumors disappear. Panc-1 cells stably expressing RhoB-F and RhoB-GG take longer to disappear (43 and 56 days, respectively). Over a 75-day period since tumor cell implantation, empty vector tumors grow to an average size of 455±197 whereas RhoB-F, RhoB-GG and RhoB-WT tumors remain undetectable (FIG. 4). Thus, RhoB-F, RhoB-GG and RhoB-WT are all potent suppressors of Panc-1 tumor growth in nude mice. The ability of RhoB to suppress Panc-1 cells tumor growth in nude mice requires prenylation by either farnesyl or geranylgeranyl since a RhoB mutant that lacks a CAAX box does not inhibit tumor growth (FIG. 4). Comparable results are obtained using A549 cells, indicating that, RhoB-F, RhoB-GG and RhoB-WT are also all potent suppressors of A549 tumor growth in nude mice.

Thus, the data disclosed herein illustrate a growth inhibitory and tumor suppressor activity of the small GTPase RhoB. Little is known about the role of RhoB in proliferation and transformation of human cancer cells. In Rat1 fibroblasts, a dominant negative form of RhoB is shown to weakly inhibit focus formation induced by oncogenic Ras. Prendergast, G. C., et al., *Oncogene* 10: 2289–2296, (1995). However, activated (GTPase-deficient [V-14]RhoB) itself lacked focus formation activity, arguing against a transforming role for RhoB. The data present herein demonstrate that in human cancer cells, RhoB is a potent inhibitor of tumor growth in nude mice. Furthermore, RhoB is also a potent inhibitor of human tumor growth in vitro as shown in both anchorage-dependent (proliferation) and anchorage-independent (transformation) assays in vitro. RhoB equipped with p53 in suppressing foci formation in several human cancer cell lines. In the same in vitro transformation assay RhoA enhances foci formation. The ability of RhoB to inhibit focus formation is not dependent on the Ras mutation status of the human cancer cell lines. Indeed, RhoB is a potent inhibitor in cancer cells where Ras is mutated (Panc-1) as well as those where Ras is wild type (Hela, C-33A and Saos-2). The tumor growth suppressor activity of RhoB is also p53-independent since some of the human cancer cell lines used have non-functional p53. Furthermore, RhoB disrupts two major signaling pathways by inhibiting IGF-1 stimulation of Akt and constitutive activation of erk2. This is consistent with its ability to inhibit proliferation and transformation. Thus, the ability of RhoB to block two signaling pathways that are involved in tumor survival and transformation may be pivotal to its tumor suppressive activity of Panc-1 cells in nude mice.

The ability of RhoB to potently antagonize transformation in vitro and in vivo shows that it is not a target for FTIs'antitumor activity in human cancer cells. Further, RhoB-F is just as potent as RhoB-GG in (a) inhibiting both human tumor growth in vitro (b) inhibiting IGF-1 stimulation of Akt and constitutive activation of erk2, and (c) inducing apoptosis and inhibiting tumor growth in nude mice. Thus, RhoB has potent antitransforming and tumor suppressor activities. Furthermore, in human cancer cells, inhibition of the farnesylation of RhoB does not contribute to the mechanism by which FTIs inhibit tumor growth.

Table 1: RhoB-WT, RhoB-F, RhoB-GG and p53, but not RhoA, Inhibit Focus Formation of Several Human Cancer Cell Lines.

Panc-1, C-33A, Hela and Saos-2 human cancer cells are transfected with the indicated expression vectors. Cells are maintained under drug selection for 2 weeks before foci are fixed, stained and counted as described under Experimental Procedures. pCMV is the control vector for RhoB-WT, RhoB-F and RhoB-GG whereas pcDNA3 for RhoA and p53. Data are representative of two independent experiments, each carried out in duplicate except for Saos-2. Similar results are obtained using a A549 human cancer cell line.

TABLE 1

| Human Cancer Cell Line | pCMV | RhoB-WT | RhoB-GG | RhoB-F | pcDNA3 | RhoA | p53 |
|---|---|---|---|---|---|---|---|
| Panc-1 #1 | 155 | 23 | 27 | 30 | 163 | 346 | 21 |
| Panc-1 #2 | 233 | 39 | 43 | 49 | 211 | 409 | 27 |
| Hela #1 | 26 | 1 | 0 | 2 | 31 | 46 | 0 |
| Hela #2 | 57 | 4 | 3 | 7 | 65 | 89 | 2 |
| C-33A #1 | 73 | 2 | 17 | 23 | 191 | 263 | 14 |
| C-33A #2 | 61 | 5 | 9 | 16 | 221 | 287 | 21 |
| Saos-2 #1 | 26 | 0 | 0 | 2 | 46 | 61 | 1 |

All publications, patents, and patent documents referred to herein are hereby incorporated in their respective entireties by reference.

The invention has been described with reference to the foregoing specific and preferred embodiments and methods. However, it should be understood that many variations may be made while remaining within the spirit and scope of the invention. Therefore, the foregoing examples are not limiting, and the scope of the invention is intended to be limited only by the following claims.

What is claimed is:

1. A method for inhibiting the growth of tumor cells in a mammal, comprising directly administering an effective amount of a nucleic acid sequence encoding a wild-type RhoB protein into the tumor cells, wherein the nucleic acid sequence is expressed in the tumor cells.

2. The method of claim 1, wherein the nucleic acid sequence is directly administered within a viral vector into the tumor cells.

3. The method of claim 1, wherein the mammal is human.

4. The method of claim 1, wherein the method further comprises administering at least one additional therapy to the mammal, wherein the therapy is selected from the group consisting of chemotherapy, radiation therapy, and therapy that selectively inhibits Ras oncogenic signaling.

5. The method of claim 1, wherein the tumor cells are cells of a solid tumor.

6. The method of claim 1, wherein the tumor cells are cancer cells of a type selected from the group consisting of pancreatic cancer, prostate cancer, breast cancer, colon cancer, rectal cancer, lung cancer, and melanoma.

7. The method of claim 1, wherein the tumor cells are cancer cells of a type selected from the group consisting of brain cancer, oral cancer, laryngeal cancer, thyroid cancer, and esophageal cancer.

8. The method of claim 1, wherein the tumor cells are lung cancer cells.

9. The method of claim 1, wherein the tumor cells are liver cancer cells.

10. The method of claim 1, wherein the tumor cells are melanoma cells.

11. The method of claim 1, wherein the nucleic acid sequence is associated with a pharmaceutically acceptable carrier.

* * * * *

UNITED STATES PATENT AND TRADEMARK OFFICE
CERTIFICATE OF CORRECTION

PATENT NO.         : 7,157,438 B2                                        Page 1 of 1
APPLICATION NO. : 10/049502
DATED              : January 2, 2007
INVENTOR(S)        : Said M. Sebti It is certified that error appears in the above-identified patent and that said Letters Patent is hereby corrected as shown below:

Column 2
Lines 19-20, "predicted to prefers a leucine. Ras proteins" should read
--predicted to be differ.
    Low molecular weight GTPases require prenylation, a lipid posttranslational modification, for their biological activity. Zhang, F.L. et al., *Annu. Rev. Biochem.*, 65:241-269, (1996). The two enzymes that catalyze these modifications for Ras and Rho GTPases are farnesyltransferase (FTase) and geranylgeranyltransferase I (GGTase I). The enzymes recognize the carboxyl terminal sequence CAAX (C=cysteine, A=aliphatic amino acid and X=any amino acid) and covalently attach a farnesyl or a geranylgeranyl to the cysteine. FTase prefers a methionine or a serine at the X position whereas GGTase I prefers a leucine. Ras proteins--.

Column 5
Line 32, "or transferring receptor" should read --or transferrin receptor--.

Column 10
Line 15, "show that RhoB-P" should read --show that RhoB-F--.

Signed and Sealed this

Fifteenth Day of May, 2007

JON W. DUDAS
*Director of the United States Patent and Trademark Office*